United States Patent [19]

Matwiyoff

[11] Patent Number: 4,915,933

[45] Date of Patent: Apr. 10, 1990

[54] MIXED COMPLEXES AS SHIFT AND CONTRAST REAGENTS IN NMR IMAGING AND SPECTROSCOPY

[75] Inventor: Nicholas A. Matwiyoff, Sante Fe, N. Mex.

[73] Assignee: The University of New Mexico, Albuquerque, N. Mex.

[21] Appl. No.: 878,651

[22] Filed: Jun. 26, 1986

[51] Int. Cl.$^4$ .......................... A61K 49/00; A61B 6/00
[52] U.S. Cl. ........................................ 424/9; 436/173; 436/806; 128/653; 128/654
[58] Field of Search .................... 424/9; 436/173, 806; 128/653, 654; 556/83

[56] References Cited

U.S. PATENT DOCUMENTS

| | | |
|---|---|---|
| 3,787,464 | 1/1974 | Neri et al. |
| 3,789,060 | 1/1974 | Goering et al. |
| 3,804,868 | 4/1974 | Chabardes et al. |
| 3,915,641 | 10/1975 | Goering et al. |
| 4,181,672 | 1/1980 | Popper et al. |
| 4,206,132 | 6/1980 | Sievers. |
| 4,419,339 | 12/1983 | Neirinckx. |
| 4,481,184 | 11/1984 | Kronauge et al. |
| 4,647,447 | 5/1987 | Gries et al. ............................. 424/9 |

OTHER PUBLICATIONS

Magnetic Resonance Imaging, vol. 2, pp. 107–112, 1984, "Relaxation Enhancement Using Liposomes Carrying Paramagnetic Species", Caride et al.

Primary Examiner—Robert J. Warden
Assistant Examiner—Stephen C. Wieder
Attorney, Agent, or Firm—Jean A. Buttmi; Charles W. Fallow

[57] ABSTRACT

Mixed anionic complexes of the type $(MW_mY_nZ_p)^{r-}$ wherein M is a paramagnetic ion; W, Y, and Z are each different ligands which chelate M; and $m+n+p \geq 2$ but preferably less than 5, with the proviso that at least two different ligands W, Y, Z are present in the complex; and provided as versatile NMR contrast and shift reagents, especially for clinical diagnostic imaging and spectroscopic procedures. In an exemplary embodiment, at least one of the ligands W, Y, Z is metabolizable by the target tissue, and at least one of the ligands W, Y, Z is substantially inert; the complex is thus tailorable to improve both physiological tolerance and tissue specificity of NMR contrast and shift reagents, while maintaining excellent contrast and shift effects for reliable and accurate results.

28 Claims, 3 Drawing Sheets

MIXED COMPLEXES AS SHIFT AND CONTRAST REAGENTS IN NMR IMAGING AND SPECTROSCOPY

BACKGROUND OF THE INVENTION

1. Field of the Invention

Paramagnetic species are commonly employed as shift or contrast reagents in nuclear magnetic resonance (NMR) studies. In clinical applications, these species are employed to alter magnetic properties in target tissue to enhance contrast and specificity in NMR imaging (MRI) and to improve spectrum resolution in NMR spectroscopy (MRS). Nacked paramagnetic species, however, are generally of limited clinical relevance in spectroscopic and imaging procedures, owing to their toxicity.

2. Discussion of Related Art

In order to exploit shift and contrast effects of these paramagnetic species in clinical diagnostic procedures, paramagnetic ions such as lanthanides, $Fe^{3+}$, $Cr^{3+}$; or $Mn^{2+}$ are typically chelated with one or more identical ligands $W$ to form simple complexes of the type $MW_x$, wherein x is $\geq 1$. Typical ligands W include bidentate and polydentate ligands such as polyphosphates, especially tripolyphosphate (PPP) and aminepolycarboxylates such as nitrilotriacetate (NTA), ethylenediaminetetraacetate (EDTA), and diethylenetriaminepentaacetate (DTPA). The complexes are structured according to their intended function: For example, $[Dy(PPP)_2]^{7-}$ is a good shift reagent for sodium spectroscopy as the favorable geometry of $Na^+$ relative to the paramagnetic dysprosium ion [Dy(III)] bound to the highly charged tripolyphosphate ligand induces large chemical shifts of the sodium ion; analogously, Gd(III) complexed with PPP to form $[Gd(PPP)_2]^{7-}$ is an effective contrast agent for proton and sodium imaging.

Unfortunately, many of these simple complexes $MW_x$ known in the art have limited clinical utility. In the case of aminepolycarboxylate ligands, the paramagnetic complexes are typically only effective as contrast reagents in sodium imaging at relatively high and potentially toxic concentrations, probably owing to weak binding of $Na^+$ or unfavorable geometry of the complex. The tripolyphosphate paramagnetic complexes $MW_x$ are effective at acceptably low concentrations, but the ligand is degraded in brain and muscle tissue, most likely by the action of pyrophosphatase, with resultant deposition of a potentially toxic paramagnetic ion in the tissue.

SUMMARY OF THE INVENTION

Figure 1A:
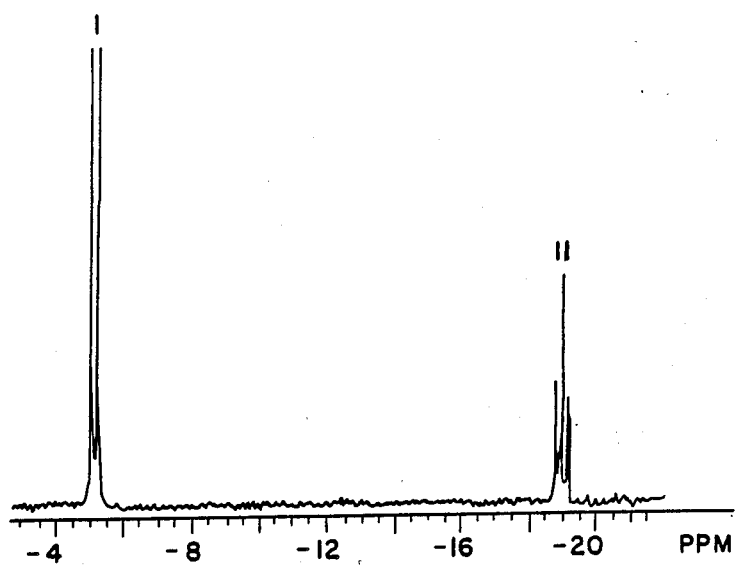
FIG. 1 illustrates $^{31}P$ spectra (121.4 MHz) of aqueous solutions of: A. 0.2M $P_3O_{10}^{5-}$ ion at pH=7.4, I=$O_3$-$PO_2P$ in $PPP^{5-}$, II=$PO_2PO_3$ in $PPP^{5-}$; B. 0.2M $[Dy(P_3O_{10})_2]^{7-}$, at pH=7.4, I=$[Dy(PPP)_2]^{7-}$, II=$PPP^{5-}$; C. 0.2M $[Dy(P_3O_{10})_2]^{7-}$ and 0.1M $P_3O_{10}^{5-}$ at pH =7.4, I=$[Dy(PPP)_2]^{7-}$, II=$PPP^{5-}$.

The invention provides anionic mixed complexes of paramagnetic ions of the formula:

$$(MW_mY_nZ_p)^{r-}$$

wherein
  M is a multivalent paramagnetic ion;
  W, Y and Z are each a different polydentate or bidentate ligand which is a chelator for the ion M;
  $m+n+p \geq 2$ but less than 5 and no more than one of m, n, or p is zero; and
  the complex has an overall negative charge r.

The complexes are useful as contrast and shift reagents for NMR spectroscopy and imaging procedures, and are particularly useful in clinical applications in mammals. Owing to the versatility imparted by the combination of two or three different ligands, the mixed complexes of the invention are far more effective in a variety of diagnostic procedures. The ligands W, Y and Z are readily selected to provide complexes tailored to fit the particular application: For example, ligands may be selected to increase or decrease tissue distribution specificity of the complex; to control toxicity of biodegradation products; to promote accumulation of the paramagnetic species in target tissue, or to othwerwise vary the properties of the complexes according to requirements.

DETAILED DESCRIPTION OF THE INVENTION

Paramagnetic species M of the mixed complexes of the invention broadly include paramagnetic ions having a cationic charge of at least two, and especially trivalent ions of the lanthanide series, particularly Dy(III) and Gd(III); other useful paramagnetic ions include Mn(II), Mn(III), Fe(III), Cu(II) and Cr(III). The particularly ion M is selected for the intended function of the complex according to generally accepted standards; for example, M is selected with reference to the properties of the ligands W, Y and Z, and with reference to the particular imaging or spectroscopic technique to be employed. The ions exhibit varying degrees of specificity and activity as paramagnetic centers of the complexes of the invention.

The ligands W, Y, and Z are bidentate (having two binding sites to the paramagnetic species M) or polydentate (having three or more binding sites to the paramagnetic species M); the net charge r on the complex comprising the ligands W, Y and, optionally, Z and the paramagnetic species M is negative, usually greater than (−3). The complexes are tailored to meet diagnostic requirements: For example, the ligands can be selected to maximize anisotropy of the paramagnetism of the ion M to enhance shift and contrast effects of the paramagnetic species; one or more of the ligands can be varied in size or lipophilicity or hydrophilicity to diminish or enhance access to extracellular spaces in vivo; one or more of the ligands can be selected to be metabolized preferentially by certain cell types to thereby temporarily accumulate the complex in a target tissue as a result of altering the net charge on the complex by elimination of a ligand; one or more of the ligands can be selected to retard the biodegradability of an otherwise metabolizable ligand; one or more the ligands can be selected to compensate for a ligand exhibiting a long term instability in vivo; further, one or more of the remaining ligands can be selected to a detoxify the central paramagnetic ion M.

The following guidelines are relevant:

for $^{23}$Na$^+$ imaging, to produce an observable effect at very low concentrations of the mixed complexes of the invention, binding at the sodium site should be strong and the distance between the Na$^+$ ion and the paramagnetic ion M should be minimized to enhance $^{23}$Na$^+$ relaxation;

for $^{23}$Na$^+$ spectroscopy, binding should also be strong but the distance between the paramagnetic M and the Na$^+$ ion(s) should be maximized to reduce $^{23}$Na paramagnetic relaxation and maintain narrow lines for high resolution in the spectrum: The paramagnetic anisotropy of the mixed complex is generally maximized to produce a large $^{23}$Na$^+$ shift at large distances;

for $^1$H imaging, any biodegradable ligand should occupy as large a number of coordination sites as possible consistent with a strong attachment of a biologically inert (relatively non-metabolizable) ligand in order to produce an observable effect at low concentrations of the complex; when the biodegradable ligand is "lost" to the targeted tissue, water molecules occupy vacated coordination sites and are subjected to paramagnetic relaxation enhancement resulting in enhanced contrast in NMR images. In such an application, the tissue specificity of the complex is conveniently controlled by selection of the ligand to be one which is metabolized by target tissue, usually degradation by enzymes peculiar to the target cells.

In an illustrative example of the invention:

For a complex $[MW_mY_nZ_p]^{r-}$ according to the invention, wherein

M is Dy(III);

W is (PPP)$^{5-}$ (m=1);

Y is (DTPA)$^{5-}$ (n=1); and p=0; to provide the complex [Dy(PPP) (DTPA)]$^{7-}$:

(PPP)$^{5-}$ provides a strong $^{23}$Na$^+$ binding site, and the illustrated complex [Dy(PPP) (DTPA)]$^{7-}$ is thus particularly useful as a high resolution agent in sodium spectroscopy or as an agent for proton imaging of those tissues capable of causing the decomposition of PPP$^{5-}$.

(PPP)$^{5-}$ exhibits a long-term instability in vivo; the instability is compensated by (DTPA)$^{4-}$, which is stable in vivo, and eventually excreted in conjunction with M, thereby avoiding toxic deposition of M in target tissue;

(PPP)$^{5-}$ is a metabolizable ligand which, in combination with the inert ligand (DTPA)$^{4-}$, allows accumulation of the complex in the target tissue for a sufficiently extended period of time to permit completion of the NMR diagnostic studies of interest.

Suitable ligands W, Y and Z broadly include those bidentate and polydentate ligands which function as strong chelating agents for the selected paramagnetic ion M. Contemplated inactive ligands (those which tend not to bind sodium or other reference ions when strongly bound to M) include the class of aminecarboxylates, exemplified by NTA (nitrilotriacetate), EDTA (ethylenediaminetetraacetate), and DTPA (diethylenetriaminepentaacetate); Schiff bases; orthohydroxyphenyl derivatives; acetylacetone derivatives; template ligands; and various other polyfunctional amino, hydroxyl and keto compounds; especially compounds such as porphyrins; 8-hydroxyquinoline; 8-hydroxyquinoline-5-sulfuric acid; aurinetricarboxylic acid; 1,2-bis(salicylideneamino) ethane; N,N'ethylenedi-(α-o-hydroxy-phenyl) glycine; hydroxamic acids and esters thereof, triethylenetetraamine, cryptates, and tetraazacyclododecanes. Contemplated active ligands (those which include potential sodium or other reference ion binding sites and combined to M potentially function as shift and contrast reagents for sodium and other reference ions) broadly include phosphates, especially tripolyphosphate and pyrophosphates; citric and aspartic acid; aminecarboxylatephosphonates; aminephosphonates; small (for example, C$_{3-20}$) peptides with carboxylate side chains; and oxalates. Ligands potentially metabolizable in vivo broadly include phosphates such as pyrophosphate (PP) and tripolyphosphate (PPP), pyridoxal, desferrioxamine, polyglutamic acid, citrates, amino acids, salicylic acid, acetoacetate, and oxalates. Suitable esterifying moieties include C$_1$-C$_6$ alkyl groups.

Particular compounds within the scope of the invention which function to optimize $^{23}$Na and $^1$H contrast and shift effects in MRI and MRS of specific normal and pathologic tissues include:

[Dy(NTA) (PPP)]$^{5-}$ and [Gd(NTA) (PPP)]$^{5-}$;

[Dy(NTA) (PP)]$^{4-}$ and [Gd(NTA) (PP)]$^{4-}$;

[Dy(EDTA) (PP)]$^{5-}$ and [Gd(EDTA) (PP)]$^{5-}$;

[Dy(EDTA) (Citrate)]$^{4-}$ and [GD(EDTA) (Citrate)]$^{4-}$; and

[Dy(DOTA) (PPP)]$^{6-}$ and [Gd(DOTA) (PPP)]$^{6-}$. (where DOTA is 1,4,7,10-tetraazacyclododecane-N,N',N'',N'''-tetraacetic acid).

Exemplary ligands organized according to function are set forth in Tables 1 through 3 as follows:

TABLE 1

POTENTIALLY BIOLOGICALLY INERT LIGANDS*

| Ligand Class | Examples |
| --- | --- |
| Aminepolycarboxylates | EDTA, DTPA, NTA, DOTA |
| Aminephosphonates | N(CH$_2$PO$_3$H$_2$)$_3$; (HO$_2$CCH$_2$)$_2$NCH$_2$PO$_3$H$_2$ |
| Macrocyclic ligands | Rifamycin S, porphyrins, tetrapyrroles, cryptates, 1,4,7,10-tetraazacyclododecane-N, N', N'', N'''-tetraacetic acid |
| Phenolates | Ethylenediamine-bis(o-hydroxyphenyl) glycine |
| Phosphates | Myoinositol hexaphosphate |

*These ligands are potentially useful in metabolizable mixed complexes by retarding degradation of the metabolizable ligand or by providing a non-toxic metabolic product comprising a paramagnetic species and the inert ligand as described supra.

TABLE 2

LIGANDS WITH POTENTIAL NA$^+$ ION BINDING SITES

| Ligand Class | Examples |
| --- | --- |
| Aminepolycarboxylates | TTHA (Triethylenetriaminehexaacetate) |
| Aminephosphonates | H$_2$O$_3$PCH$_2$—N(CH$_2$CO$_2$H)$_2$ |
| Carboxylic acids | Citric, oxalic |
| Phosphates | Pyrophosphate, tripolyphosphate, myoinositol hexaphosphate |

TABLE 3

POTENTIALLY METABOLIZABLE LIGANDS

| Ligand Class | Examples |
| --- | --- |
| Amino acids | Aspartic, aminomalonic |
| Barbiturate Derivatives | Aminobarbituric acid - N,N-diacetic acid |

TABLE 3-continued
POTENTIALLY METABOLIZABLE LIGANDS

| Ligand Class | Examples |
| --- | --- |
| | HN——CO |
| | \| \| |
| | CO HC—N(CH$_2$CO$_2$H)$_2$ |
| | \| \| |
| | HN——CO |
| Carboxylic acids | Citric, salicylic, acetoacetic, oxalic |
| Hydroxamates | Benzhydroxamic acid, desferrioxamine B |
| Phenolates | N-2,3-Dihydroxybenzoylglycine |
| Phosphates | Pyrophosphate, tripolyphosphate, trimetaphosphate, diphosphoglycerate, phytate. |

The mixed complexes of the invention are usefully prepared in analogous manner to the simple complexes described in the prior art. Broadly, the mixed complexes are readily prepared by dissolving an inorganic salt of the paramagnetic ion M (conveniently the corresponding chloride or oxide) in a first ligand solution, followed by addition of a second ligand and third ligand if desired, or by dissolving the salt in a solution of combined ligands; alternatively, the ligand is dissolved in a solution of a salt of the ion M, with addition of a second ligand to the solution, followed by a third ligand if desired. The mixed complexes are also conveniently prepared by combining solutions of simple complexes [e.g., $(MW)^{r-}, (MY)^{r-}$] or by combining separate solutions of paramagnetic ion M and individual ligands.

As will be apparent to those skilled in the art, an extensive selection of ligands to achieve a variety of results is within the scope of the invention. Broadly, the complexes are tailored to optimize chemical shift and/or contrast effects for target tissue while minimizing or capitalizing upon tissue biodegradation of or decomposition of a particular ligand depending upon the desired result, while simultaneously avoiding formation of toxic by-products. The complexes are tailorable over a broad range of compositions to optimize $^{23}NA^+$ and/or $^1H$ contrast or shift effects in MRI and MRS studies of normal and pathologic tissues, both in vitro and in vivo, as well as $^{31}P$, $^{13}C$ (termed herein "reference ions") and related spectroscopic and imaging procedures. Parameters of particular interest for clinical applications include physiological tolerance (toxicity); physiological stability (decomposition rate in vivo or in vitro); nature and strength of the interactions of the complex with water protons and sodium ions in vivo, and effect on the nuclear magnetic resonance of water protons and sodium ion in imaging and spectroscopy on tissues in vivo and in vitro (for $^{23}Na^+$ and $^1H^+$ imaging and spectroscopy). The complexes are generally designed to have a high physiological tolerance; to effect a larger or smaller region of specific body tissue according to the influence of the ligands W, Y, Z on the paramagnetism of the ion M and the translation of this paramagnetism to the water molecules, sodium ions, or other target; and to accumulate in different types of tissue according to the ligands selected. The ligands are usually chosen to selectively accumulate in diseased or dead tissue cells (infarcts) or in rapidly dividing cells (tumors), or in normal cells, as desired; the tissue contrast obtained is a function of tissue ability to accommodate the mixed complexes of the invention in extracellular or intracellular spaces and to degrade particular ligands, which in turn is a function of flow, diffusion, interstitial spaces, lipophilicity or hydrophilicity of individual ligands and the complex as a whole, enzyme activities, and other factors. Properly adapted mixed complexes permit differentiation between normal and diseased tissue, documentation of methobolic changes induced by radiation damage, hypoxia, ischemia, and hypoglycemia, evaluation of therapeutic agents on living tissue, establishment of parameters for normal tissue, an measurement of a large variety of physiological functions.

The mixed complexes of the invention are employed according to known prior art procedures; the complexes are typically clinically administered intravenously or orally, with the amounts administered being dependent upon the properties of the particular complex, the target tissue, the specific diagnostic procedure, and other factors customarily considered in analogous conventional procedures. The complexes are further useful in non-clinical or laboratory diagnostic procedures such as those for the differentiation of tissue in vitro, and other applications. Descriptions of such procedures are common in the art; exemplary are those set forth in Lauffer, et al, *Magn. Res. Imaging* 3:11-16, 1985; Carr, ibid, 17-25, 1985; Runge, et al, ibid, 27-35, 1985; Runge, et al, ibid, 43-55, 1985; and Wesley et al, ibid, 57-64, 1985, all incorporated herein by reference.

The following Examples are illustrative of the practice of the invention.

PREPARATION OF SIMPLE AND MIXED COMPLEXES

Example I.

Preparation of complexes by dissolving solid DyCl$_3$ (hydrated or unhydrated) in solutions of individual and/or combined ligands.

A. Dy(P$_3$O$_{10}$)$^{-2}$

1. A 0.1M solution was prepared by dissolving 1.885 gms (0.005 moles) of DyCl$_3$.6H$_2$O in 25 ml of 0.2M P$_3$O$_{10}^{-5}$ (see VI.A). While adding the DyCl$_3$.6H$_2$O, the pH was maintained between 5 and 8. Finally, the total volume was brought to 50 ml, and the pH was adjusted to 7.

B. [Dy(P$_3$O$_{10}$)$_2$]$^{7-}$

1. A 0.1M solution was prepared by dissolving 1.885 gms (0.005 moles) of DyCl$_3$.H$_2$O in 25 ml of 0.4M P$_3$O$_{10}^{-5}$ (see VI.E). While adding the DyCl$_3$.6H$_2$O, the pH was maintained between 6 and 8. Finally, the total volume was brought to 50 ml, and the pH was adjusted to 7.

C. Dy(EDTA)$^{-1}$

1. A 0.1M solution was prepared by dissolving 1.885 gms (0.005 moles) of DyCl$_3$.6H$_2$O in 25 ml of 0.2M EDTA (see VI.B). While adding the DyCl$_3$.6H$_2$O, the pH was maintained above 6. Finally, the total volume was brought to 50 ml, and the pH was adjusted to 7.

D. Dy(EDTA)$_2^{-5}$

1. A 0.1M solution was prepared by dissolving 1.885 gms (0.005 moles) of DyCl$_3$.6H$_2$O in 25 ml of 0.4M EDTA (see VI.F). While adding the DyCl$_3$.6H$_2$O, the pH was maintained above 6. Finally, the total volume was brought to 50 ml, and the pH was adjusted to 7.

E. Dy(EDTA) (P$_3$O$_{10}$)$^{-6}$

1. A 0.1M solution was prepared by dissolving 1.885 gms (0.005 moles) of DyCl$_3$.6H$_2$O in 25 ml of warm 0.2M EDTA (see VI.B). During the addition, the pH was maintained above 6, followed by the addition of 1.839 gms (0.005 moles) of Na$_5$P$_3$O$_{10}$. After this the volume was brought to 50 ml while maintaining the pH at 7.

F. Dy(EDTA) (P$_2$O$_7$)$^{-5}$

1. A 0.1M solution was prepared by dissolving 1.885 gms (0.005 moles) of DyCl$_3$·6H$_2$O in 25 ml of warm 0.2M EDTA (see VI.B). During the addition, the pH was maintained above 6, followed by the addition of 1.11 gms (0.005 moles) of Na$_2$H$_2$P$_2$O$_7$. after this, the volume was brought to 50 ml while maintaining the pH at 7.

G. Dy[N(CH$_2$PO$_3$)$_3$](P$_3$O$_{10}$)$^{-8}$

1. A 0.1M solutiuon was prepared by dissolving 1.885 gms (0.005 moles) of DyCl$_3$·6H$_2$O in 25 ml of 0.2M solution of nitrilotris (methylene) triphosphonic acid (see VI.D). During the addition, the pH was maintained above 6, followed by the addition of 1.839 gms. (0.005 moles) of Na$_5$P$_3$O$_{10}$. After this, the volume was brought to 50 ml while maintaining the pH at 7.

H. [Dy(EDTA) (P$_2$O$_7$) (P$_3$O$_{10}$)]$^{-10}$

1. A 0.1M solution is prepared by dissolving 1.885 gms (0.005 moles) of DyCl$_3$·6H$_2$O and 1.861 gms (0.005 moles) of disodium ethylenediaminetetraacetic acid dihydrate in 25 ml of 0.2M P$_3$O$_{10}$$^{-5}$ (see VI A). While adding the salts the pH is kept between 6 and 8, and then 1.11 gms (0.005 moles) of Na$_2$H$_2$P$_2$O$_7$ are added to the resulting solution. After this the volume is brought to 50 ml while maintaining the pH at 7.

EXAMPLE II.

Preparation of solutions of complexes by dissolving a ligand in a solution containing another ligand and/or Dy$^{3+}$.

A. Dy(P$_3$O$_{10}$)$^{-2}$

1. A 0.1M solution was prepared by dissolving 1.835 gms (0.005 moles) of Na$_5$P$_3$O$_{10}$ in 25 ml of 0.2M solution of Dy$^{3+}$ (see V.A or V.B). The total volume was brought to 50 ml with distilled H$_2$O while adjusting pH to 7.

B. Dy(P$_3$O$_{10}$)$_2$$^{-7}$ or [Dy(PPP)$_2$]$^{7-}$

1. A 0.1M solution was prepared by dissolving 3.679 gms of Na$_5$P$_3$O$_{10}$ (0.01 moles) in 25 ml of 0.2M solution of Dy$^{3+}$ (see V.A or V.B). The total volume was brought to 50 ml with distilled H$_2$O while adjusting the pH to 7.

C. Dy(EDTA)$^{-1}$

1. A 0.1M solution was prepared by dissolving 1.86 gms (0.005 moles) of Na$_2$C$_{10}$H$_{14}$O$_8$N$_2$2H$_2$O (disodium ethylenediaminetetraacetate dihydrate) in 25 ml of a warm 0.2M solution of Dy$^{3+}$ (see V.A. or V.B). The total volume was brought to 50 ml with distilled H$_2$O while adjusting the pH to 7.

D. (Dy(EDTA)$_2$$^{-5}$

1. A 0.1M solution was prepared by dissolving 3.722 gms (0.01 moles) of Na$_2$C$_{10}$H$_{14}$O$_8$N$_2$2H$_2$O (disodium ethylenediaminetetraacetate dihydrate) in 25 ml of 0.2M solution of Dy$^{3+}$ (see V.A or V.B). The total volume was brought to 50 ml with distilled H$_2$O while adjusting the pH to 7.

E. Dy(EDTA) (P$_3$O$_{10}$)$^{-6}$

1. A 0.1M solution was prepared by dissolving 1.86 gms (0.005 moles) of Na$_2$C$_{10}$H$_{14}$O$_8$N$_2$·2H$_2$O (EDTA) in 25 ml of warm 0.2M Dy$^{3+}$ (see V.A or V.B). The pH of the solution was adjusted to 7, and 1.835 gms (0.005 moles) of Na$_5$P$_3$O$_{10}$ was added while bringing the total volume to 50 ml and readjusting pH to 7.

F. Dy(EDTA) (P$_2$O$_7$)$^{-5}$

1. A 0.1M solution was prepared by dissolving 1.86 gms (0.005 moles) of Na$_2$C$_{10}$H$_{14}$O$_8$N$_2$·2H$_2$O (EDTA) in 25 ml of warm 0.2M Dy$^{3+}$ (see V.A. or V.B.). The pH of the solution was adjusted to 7, and 1.11 gms (0.005 moles) of Na$_2$H$_2$P$_2$O$_7$ was added while bringing the total volume to 50 ml and adjusting pH to 7.

G. Dy[N(CH$_2$PO$_3$)$_3$](P$_3$O$_{10}$)$^{-8}$

1. A 0.1M solution was prepared by dissolving 2.99 gms of a 50% by weight solution nitrilotris(methylene)-triphosphonic acid in H$_2$O in 25 ml of 0.2M Dy$^{3+}$ (see V.A or V.B). The pH of the solution was adjusted to 7, and 1.835 gms (0.005 moles) of Na$_5$P$_3$O$_{10}$ was added while bringing the volume up to 50 ml and readjusting the pH to 7.

EXAMPLE III.

Preparation of mixed complexes by mixing solutions of individual pure complexes.

A. Dy(P$_3$O$_{10}$) (EDTA)$^{-6}$

1. A 0.1M solution was prepared by mixing 25 ml of 0.2M Dy(P$_3$O$_{10}$)$_2$$^{-7}$ (see IV.B) with 25 ml of 0.2M Dy(EDTA)$_2$$^{-5}$ (see IV.D) while stirring.

EXAMPLE IV.

Preparation of solution of individual complexes by mixing solutions of Dy$^{3+}$ and solutions of individual ligands.

A. Dy(P$_3$O$_{10}$)$^{-2}$

1. A 0.1M solution was prepared by mixing equal volumes of 0.2M Dy$^{3+}$ (see V.A or V.B) and 0.2M P$_3$O$_{10}$$^{-5}$ solution (see VI.A). The solution was stirred for one hour.

B. Dy(P$_3$O$_{10}$)$_2$$^{-7}$

1. A 0.1M solution was prepared by mixing equal volumes of 0.4M P$_3$O$_{10}$$^{-5}$ solution (see VI.E) and 0.2M Dy$^{3+}$ solution (see V.A or V.B). The solution was stirred for one hour.

C. Dy(EDTA)$^{-1}$

1. A 0.1M solution was prepared by mixing equal volumes of 0.2M EDTA solution (see VI.B) and 0.2M Dy$^{3+}$ solution (see V.A or V.B). The solution was stirred for one hour.

D. Dy(EDTA)$_2$$^{-5}$

1. A 0.1M solution was prepared by mixing equal volumes of 0.2M Dy$^{3+}$ solution (see V.A and V.B) and 0.4M EDTA solution (see VI.F). The solution was stirred for one hour.

E. Dy[N(CH$_2$PO$_3$)$_3$]$^{-3}$

1. A 0.1M solution was prepared by mixing equal volumes of 0.2M Dy$^{3+}$ solution (see V.A or V.B) and 0.2M nitrilotris(methylene)triphosphonic acid solution (see VI.D). The solution was stirred for one hour.

F. Dy(EDTA) (P$_2$O$_7$)$^{-5}$

1. A 0.066M solution was prepared by mixing equal volumes of 0.2M Dy$^{3+}$ solution (see V.A or V.B) and 0.2M EDTA solution (see VI.B). This was followed by the addition of an equal amount of 0.2M P$_2$O$_7$$^{-5}$ (see VI.C) solution. The solution was stirred for one hour.

G. Dy[N(CH$_2$PO$_3$)$_3$] (P$_3$O$_{10}$)$^{-8}$

1. A 0.066M solution was prepared by mixing equal volumes of 0.2M Dy$^{3+}$ solution (see V.A or V.B) and 0.2M N(CH$_2$PO$_3$)$_3$$^{-6}$ solution (see VI.D). This was followed by the addition of an equal volume of a 0.2M P$_3$O$_{10}$$^{-5}$ solution (see VI.A). The solution was stirred for one hour.

EXAMPLE V.

Preparation of solutions of Dy$^{3+}$ in H$_2$O

A. From Dy$_2$O$_3$

1. A 0.2M solution was prepared by dissolving 1.492 gms (0.004 moles) of Dy$_2$O$_3$ in 20 ml of 6N HCL and adding H₂O to bring the total volume to 20 ml while adjusting the pH to 7.

B. From DyCl₃ (hydrated or unhydrated)

1. A 0.2M solution was prepared by dissolving 3.7695 gms of DyCl₃.6H₂O (0.01 mole) in 50 ml of H₂O while adjusting the pH to 7.

EXAMPLE VI.

Preparation of solutions of individual ligands.

A. $P_3O_{10}^{-5}$

1. A 0.2M solution was prepared by dissolving 3.679 gms (0.01 moles) of Na₅P₃O₁₀ in distilled H₂O. The total volume was brought to 50 ml while adjusting the pH to 7.

B. $EDTA^{-4}$

1. A 0.2M solution prepared by dissolving 3.722 gms (0.01 moles) of disodium ethylene diaminetetraacetic acid dihydrate (Na₂C₁₀H₁₄O₈N₂2H₂O) in warm distilled H₂O. The total volume was brought to 50 ml while adjusting the pH to 7.

C. $P_2O_7^{-4}$

1. A 0.2M solution was prepared by dissolving 2.22 gms (0.01 mole) of Na₂H₂P₂O₇ (disodium pyrophosphate) in warm distilled H₂O. The total volume was brought to 50 ml while adjusting the pH to 7.

D. $N(CH_2PO_3)_3^{-6}$

1. A 0.2M solution was prepared by dissolving 5.98 gms of a 50% by weight solution of nitrilotris(methylene)triphosphonic acid in H₂O, and further dissolving the acid with distilled H₂O up to a volume of 50 ml while adjusting the pH to 7.

E. $P_3O_{10}^{-5}$

1. A 0.4M solution was prepared by dissolving 7.358 gms (0.02 moles) of Na₅P₃O₁₀ in distilled H₂O and bringing the volume to 50 ml while adjusting the pH to 7.

F. $EDTA^{-4}$

1. A 0.4M solution was prepared by dissolving 7.444 gms (0.02 moles) of disodium ethylenediamine tetraacetate in warm distilled H₂O. The total volume was brought to 50 ml while adjusting the pH to 7.

CHARACTERIZATION OF SIMPLE COMPLEXES OF THE TYPE $MW_x$ COMPARISON EXAMPLE

EXAMPLE VII.

The Simple Complex, $[Dy(PPP)_2]^{7-}$ (or $[Dy(P_3O_{10})_2]^{7-}$)

Figure 1B:
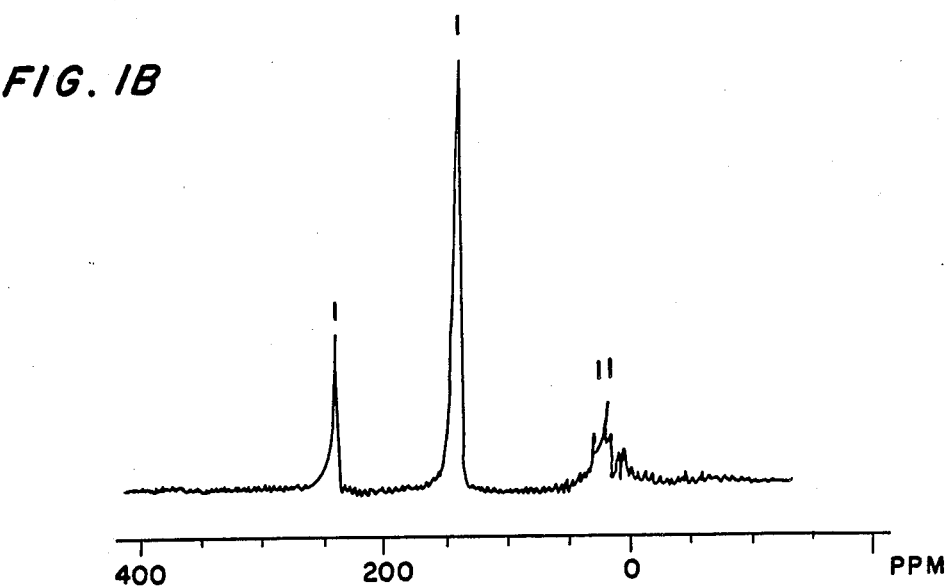
Figure 1C:
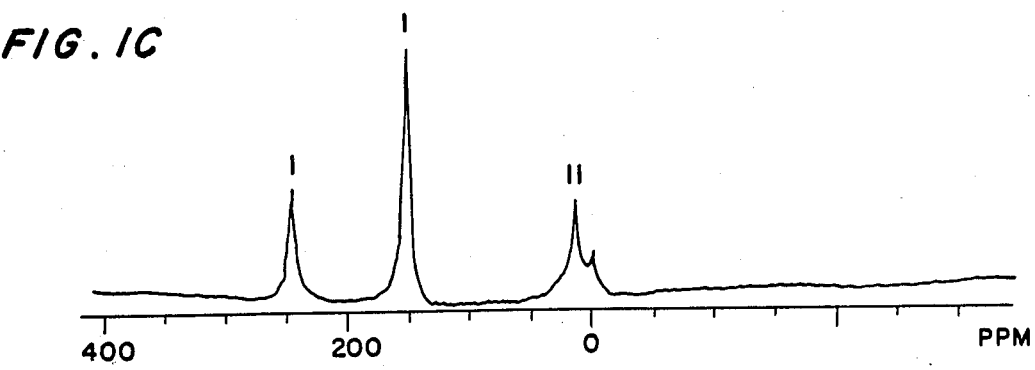

A. The ³¹P NMR spectra of aqueous solutions of $PPP^{5-}$ and $[Dy(PPP)_2]^{7-}$ ions according to Examples II B and VI A are illustrated in FIG. 1. As is apparent from the spectra, coordination of $PPP^{5-}$ to the paramagnetic Dy(III) ion results in large downfield pseudo-contact and contact shifts (+150.1 and 233.1 ppm) of the ³¹P resonances which maintain an intensity ratio of 1:2 when coordinated.

Spectrum 1B is consistent with an equilibrium constant of ~800M⁻¹ for the following reaction

(1)

in which chemical exchange between $PPP^{5-}$ and $[Dy(PPP)_2]^{7-}$ is slow on the NMR time scale. Spectrum 1C also demonstrates slow exchange for these entities and provides no direct evidence for the formation of a $[Dy(PPP)_3]^{12-}$ ion. Chemical exchange between $PPP^{5-}$ and $[Dy(PPP)_2]^{7-}$ with a maintenance of 1:2 ratio of the intensity of the ³¹P resonances of the latter is consistent with the occurrence of a fluxional process.

Figure 3A:
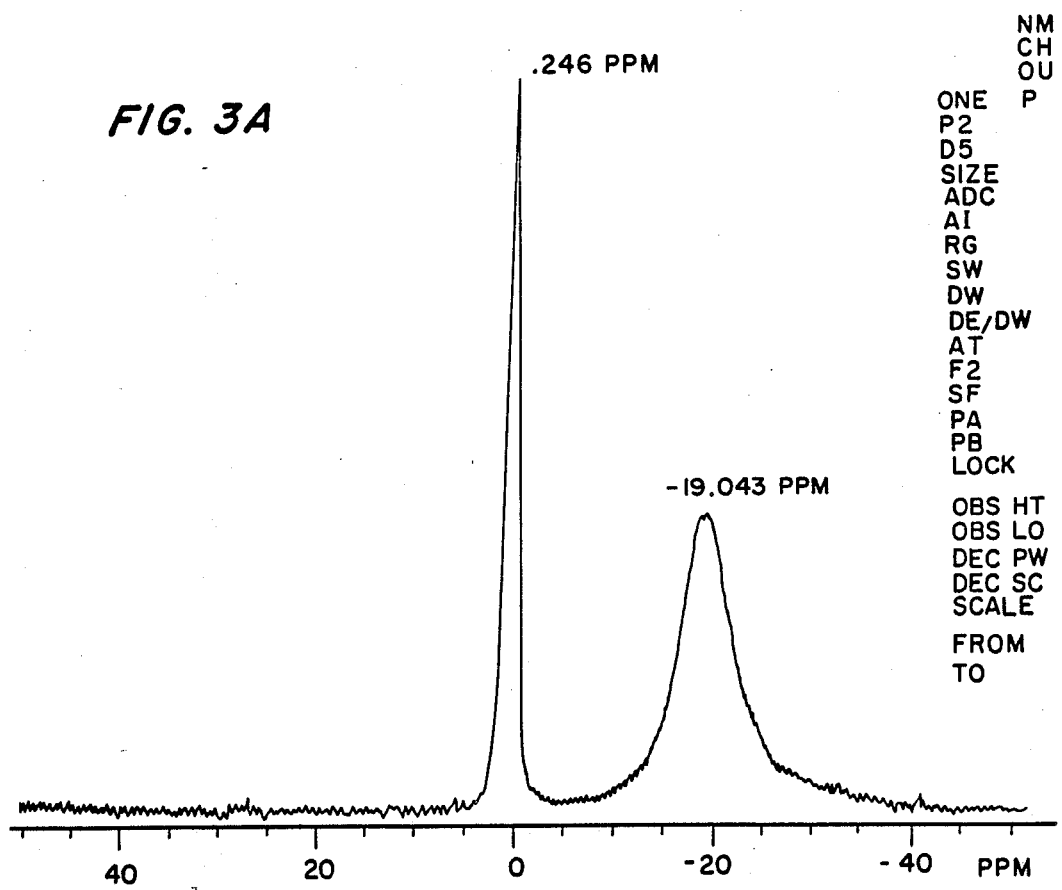
FIG. 3(A) illustrates the $^{23}Na$ NMR (79.4 MHz) spectrum of an erythrocyte suspension made 5.0 mM in $[Dy(P_3O_{10})_2]^{7-}$: The $^{23}Na$ resonance at 2.5 ppm is due to intracellular $Na^+$ ion and that at −19 ppm is due to extracellular $Na^+$ ion.
Figure 3B:
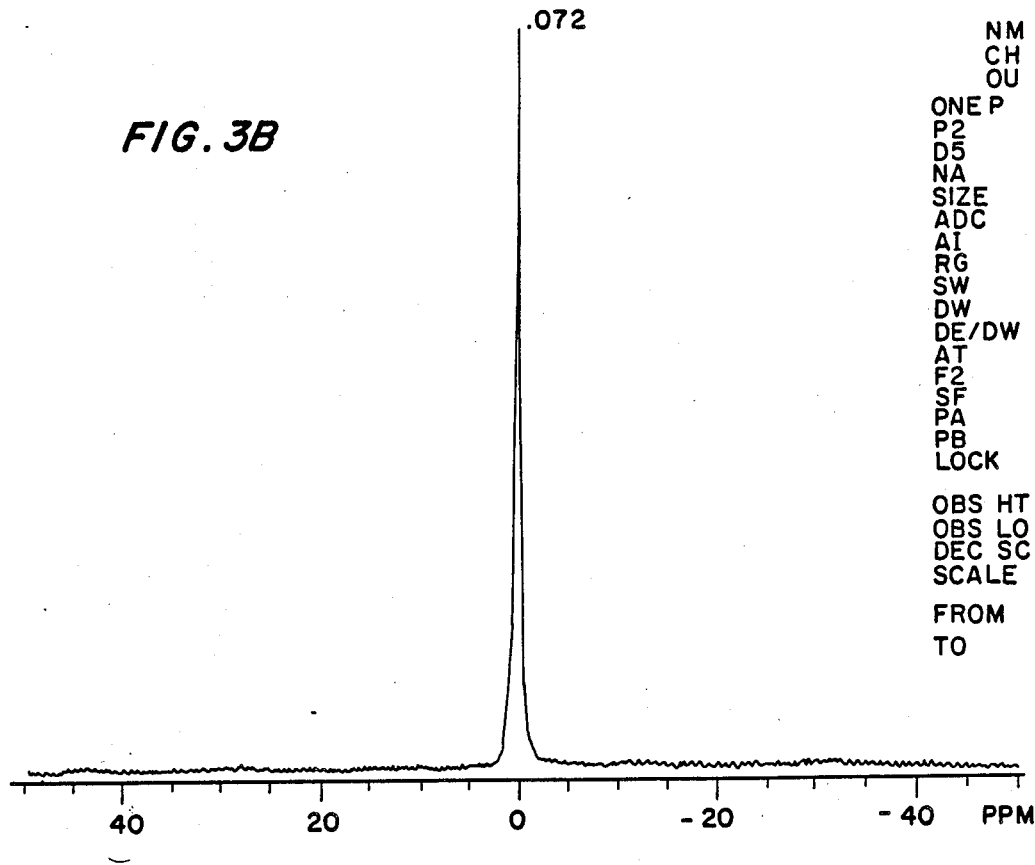
FIG. 3(B) illustrates the $^{23}Na$ NMR (79.4 MHz) spectrum of the erythrocyte suspension of FIG. 3(A) before addition of the complex: The signal at 0 ppm is the average of extra and intracellular sodium ion.

B. The addition of $[Dy(PPP)_2]^{7-}$ from Example VII A (final concentration, 5 mM) to an erythrocyte suspension (isotonic choline buffer suspension, 80% hematocrit) results in the immediate appearance of two Na⁺ ion resonances (chemical shift −20. ppm) in the ²³Na NMR spectra attributable to unshifted intracellular Na⁺ ion and extracellular Na⁺ ion which experiences a pseudo-contact shift via the formation of a weak complex, $\{Na[Dy(PPP)_2]\}^{6-}$. These spectra are time invariant over a 36 hour period (FIG. 3A). In addition to affecting the chemical shift of the extracellular Na⁺ ion, the $[Dy(PPP)_2]^{7-}$ agent also changes the relaxation properties of the Na⁺ ion and water. The line width of the extracellular Na⁺ ion changes from −40 Hz (full width at half-maximum height) in the absence of the reagent to 90 Hz in its presence. This pronounced effect on the apparent T₂ relaxation time from 25 milliseconds to 9 milliseconds. The $[Dy(PPP)_2]^{7-}$ shift reagent reduces the T₁ and T₂ values of extracellular water protons by more than a factor of three. The precise effect of the agent on the relaxation times is a function of the ratio of [Na⁺ ion]:[agent] and of [H₂O]:[agent].

CHARACTERIZATION OF MIXED COMPLEXES ACCORDING TO THE INVENTION

Example VIII.

The Mixed Complex, $[Dy(EDTA)(PPP)]^{6-}$ (or $[Dy(EDTA)(P_3O_{10})]^{6-}$)

Figure 2A:
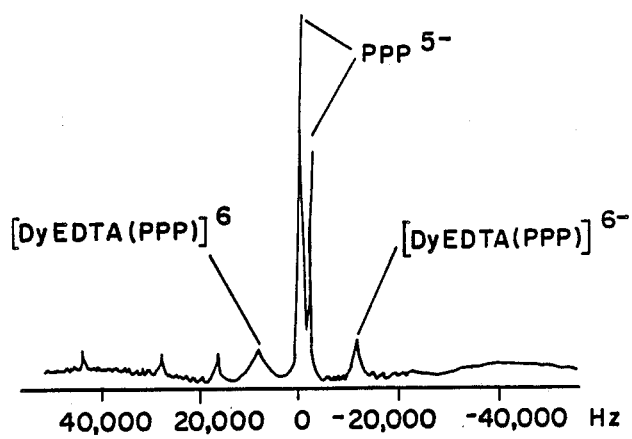
FIG. 2 illustrates $^{31}P$ NMR spectra (121.5 MHz) of aqueous solutions containing Dy(III), $EDTA^{4-}$, and $PPP^{5-}$ ions.
Figure 2B:
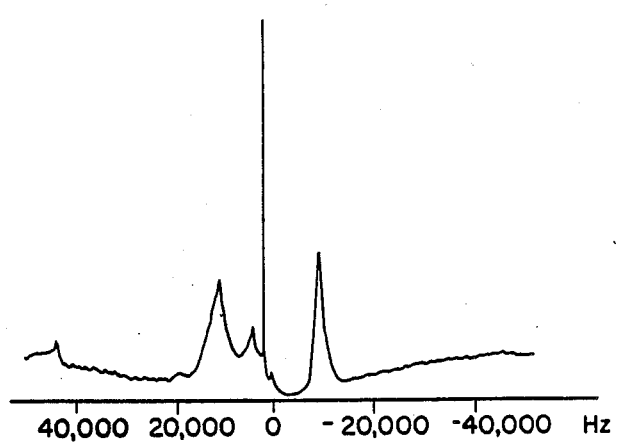
Figure 2C:
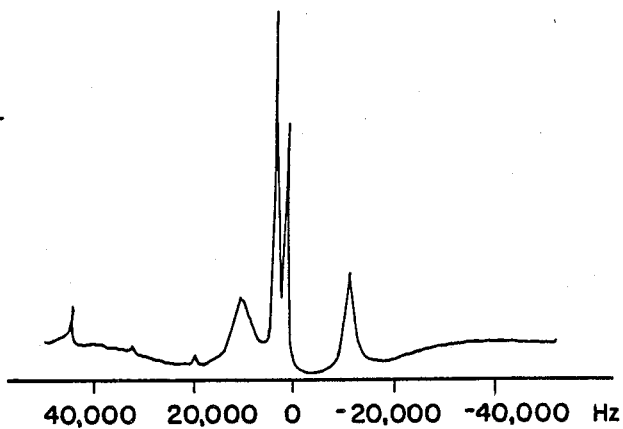

A. The ³¹P NMR spectra (FIG. 2) of an aqueous solution containing equal concentrations of Dy³⁺ ion and $EDTA^{4-}$ ion, and variable amounts of the $PPP^{5-}$ ion according to Example III A at pH 7.4 demonstrate that the mixed $[Dy(EDTA)(PPP)]^{6-}$ complex exists in solution. The relative areas of the signals assigned to $PPP^{5-}$ and the $[Dy(EDTA)(PPP)]^{6-}$ ion are consistent with an equilibrium constant of approximately 20M⁻¹ for the following reaction at the higher concentrations

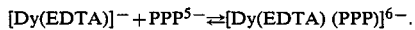

This is contrasted with an approximate equilibrium constant of >800M⁻¹ measured by ³¹P NMR for the reaction of the analogous $[Dy(PPP)_2]^{7-}$ complex

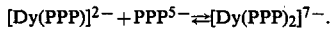

The smaller formation constant for $[Dy(EDTA)(PPP)]^{6-}$ was not predictable based on gross considerations of charge repulsion effects. However, more important than overall charge is the effect on the residual binding capacity of Dy(III) of the partial charge transferred to Dy(III) in the hexadentate $[Dy(EDTA)]^-$ complex compared to the bidentate $[Dy(PPP)]^{2-}$ complex. Steric and statistical considerations also affect the relative values of the formation constants.

B. An isotonic suspension (isotonic choline buffer) of erythrocytes (80% hematocrit) was made 5 mM with respect to the $[Dy(EDTA)(PPP)]^{6-}$ ion complex from Example VII A. Two Na⁺ ion resonances appeared in the ²³Na⁺ NMR spectrum, with the extracellular resonance appearing 3.0 ppm upfield from that of the intracellular Na⁺ ion. This is contrasted with a shift of ~20 ppm induced between these two resonances by

[Dy(PPP)₂]⁷⁻ at 5 mM (Example VII.B) and with no shift induced by [Dy(EDTA)]⁻ at concentrations up to 100 mM. The lack of a [Dy(EDTA)]⁻ ion-induced $^{23}$Na shift is probably attributable to the weakness of the {Na⁺[Dy(EDTA)]⁻} complex and a small anisotropy of the paramagnetic susceptibility of the [Dy(EDTA)]⁻ complex ion. The smaller $^{23}$Na⁺ ion shift of the {Na⁺[Dy(EDTA) (PPP)]⁶⁻}⁵⁻ complex probably resides in both geometric and anisotropic paramagnetic susceptibility factors. This shift reagent lowers the relaxation times of extracellular sodium ion by more than a factor of two, and those of the protons of extracellular water by more than a factor of five.

EXAMPLE IX.

The Mixed Complex, Dy[N(CH₂PO₃)₃] [PPP]⁸⁻ or Dy[N(CH₂PO₃)₃] [P₃O₁₀]⁸⁻

A. The mixed complex, Dy[N(CH₂PO₃)₃] [PPP]⁸⁻ in aqueous solution prepared according to Example II G exhibited a large number of paramagnetically shifted $^{31}$P resonances which are distinct from the $^{31}$P resonances of the ligands themselves or the simple complexes Dy[N(CH₂PO₃)₃]³⁻ and Dy(PPP)₂⁷⁻.

B. The addition of this complex (final concentration, 5 mM) to an erythocyte suspension (isotonic choline buffer, 80% hematocrit) resulted in the immediate appearance of two Na⁺ ion resonances. The agent reduced the relaxation times of extracellular Na⁺ ion by more than a factor of four and those of the proton in extracellular water by more than a factor of four.

What is claimed is:

1. In a nuclear magnetic resonance diagnostic method of the type wherein a paramagnetic species is employed in an amount sufficient to observably alter the magnetic properties of a reference ion in vivo or in vitro, the improvement comprising employing as the paramagnetic species an anionic mixed complex of a paramagnetic ion of the formula:

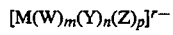

$[M(W)_m(Y)_n(Z)_p]^{r-}$ wherein
M is a paramagnetic ion;
W, Y, and Z are each a different bidentate or polydentate ligand which is a chelating agent for the ion M;
m+n+p≧2 but less than 5, and no more than one of m, n, or p is zero; and
the complex has an overall negative charge r−.

2. The method of claim 1, wherein the reference ion is a sodium ion.

3. The method of claim 2, wherein the paramagnetic ion M is selected from the group consisting of paramagnetic lanthanide ions, Mn(II), Mn(III), Fe(II), Cu(II) and Cr(III).

4. The method of claim 3, wherein the paramagnetic ion M is Dy(III) or Gd(III).

5. The method of claim 2, wherein each of the ligands is independently selected from the group consisting of aminecarboxylates, Schiff bases, aminecarboxylatephosphonates, porphryins, cryptates, hydroxamates, polyacetates, tetraazacyclododecanes, phosphates, phosphonates, aminephosphonates, C₃-C₂₀-peptides, amino acids, and salicylic acid, acetoacetic acid, oxalic acid, citric acid, aspartic acid and esters thereof.

6. The method of claim 2, wherein at least one of the ligands is metabolizable in vivo.

7. The method of claim 6, wherein the metabolizable ligand is pyrophosphate; tripolyphosphate; an amino acid; pyridoxal; desferrioxamine; polyglutamic acid; or acetoacetic acid, oxalic acid, citric acid, salicylic acid, or an ester thereof.

8. The method of claim 6, wherein the ligand metabolizable in vivo is preferentially metabolized by cells in a target tissue.

9. The method of claim 6, wherein at least one of the ligands is metabolically inert in vivo.

10. The method of claim 9, wherein the inert ligand is selected from the group consisting of aminecarboxylates, porphyrins, cryptates, tetraazacyclododecanes, cyclictetrapyrroles, aminecarboxylatephosphonates, aminephosphonates, and phosphates.

11. The method of claim 9, wherein the ligand metabolizable in vivo is selected from the group consisting of pyrophosphate; tripolyphosphate, amino acids, pyridoxal, desferrioxamines, polyglutamic acid, acetoacetic acid, oxalic acid, citric acid, salicylic acid, acetoacetates, oxalates, salicylates, and citrates; and the ligand metabolically inert in vivo is selected from the group consisting of aminecarboxylates, aminecarboxylatephosphonates, aminephosphonates, porphyrins, cryptates, tetraazocyclododecanes, cyclic tetrapyrroles, and phosphates.

12. The method of claim 6, wherein the metabolizable ligand is tripolyphosphate or pyrophosphate.

13. The method of claim 2, wherein at least one of the ligands is metabolically inert in vivo.

14. The method of claim 13, wherein the inert ligand is selected from the group consisting of aminecarboxylates, porphyrins, cryptates, tetraazacyclododecanes, cyclictetrapyrroles, aminecarboxylatephosphonates, aminephosphonates, and phosphates.

15. The method of claim 2, wherein at least one of the ligands is tripolyphosphate or pyrophosphate and at least one of the ligands is an aminecarboxylate.

16. The method of claim 15, wherein the aminecarboxylate is nitrilotriacetate, ethylenediaminetetraacetate, diethylenetriaminepentaacetate, or 1,4,7,10-tetraazacyclododecane-N,N',N'', N'''-tetraacetic acid.

17. The method of claim 2, wherein the complex is adapted to alter the magnetic resonance properties of sodium ions or water protons in vivo.

18. The method of claim 2, wherein r is at least three.

19. The method of claim 2, wherein W is (PPP) and Y is (DTPA), m is one, n is one and p is zero.

20. The method of claim 2, wherein W is (NTA), Y is (PPP), m is one, n is one and p is zero.

21. The method of claim 2, wherein W is (NTA) or (EDTA), Y is (PP) or citrate, m is one, n is one and p is zero.

22. The method of claim 21, wherein M is Dy or Gd.

23. The method of claim 2, wherein the diagnostic method is a nuclear magnetic resonance imaging procedure, and the paramagnetic species is employed as a contrast reagent.

24. The method of claim 2, wherein the diagnostic method is a nuclear magnetic resonance spectroscopic procedure, and the paramagnetic species in employed as a shift reagent.

25. The method of claim 24, wherein the shift reagent is [Dy(DTPA) (PPP)]⁶⁻ or [Dy(ETPA) (PPP)]⁶⁻.

26. The method of claim 24, wherein the shift reagent is [Dy(PPP) (1,4,7,10-tetraazacyclododecane-N, N', N'', N'''-tetraacetate)]⁶⁻.

27. The method of claim 2, wherein the complex is adapted to alter the magnetic resonance properties of sodium ions in vitro.

28. The method of claim 1, wherein the reference ion is a water proton.

* * * * *